(12) United States Patent
Bell

(10) Patent No.: US 10,332,810 B2
(45) Date of Patent: Jun. 25, 2019

(54) PROCESS MODULES INTEGRATED INTO A METROLOGY AND/OR INSPECTION TOOL

(71) Applicant: KLA-Tencor Corporation, Milpitas, CA (US)

(72) Inventor: Bobby R. Bell, San Francisco, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 15/792,705

(22) Filed: Oct. 24, 2017

(65) Prior Publication Data

US 2018/0114732 A1   Apr. 26, 2018

Related U.S. Application Data

(60) Provisional application No. 62/412,199, filed on Oct. 24, 2016.

(51) Int. Cl.
| | | |
|---|---|---|
| *H01L 21/00* | (2006.01) | |
| *H01L 21/66* | (2006.01) | |
| *H01L 21/67* | (2006.01) | |
| *G01N 21/95* | (2006.01) | |

(52) U.S. Cl.
CPC ......... *H01L 22/12* (2013.01); *G01N 21/9501* (2013.01); *H01L 21/67288* (2013.01); *H01L 22/20* (2013.01); *H01L 22/34* (2013.01)

(58) Field of Classification Search
CPC .... H01L 22/12; H01L 22/20; H01L 21/67288
See application file for complete search history.

(56) References Cited

U.S. PATENT DOCUMENTS

| | | | |
|---|---|---|---|
| 4,232,063 A | 11/1980 | Rosler et al. | |
| 4,842,683 A | 6/1989 | Cheng et al. | |
| 5,215,619 A | 6/1993 | Cheng et al. | |

(Continued)

FOREIGN PATENT DOCUMENTS

| | | |
|---|---|---|
| WO | 99/39183 | 8/1999 |
| WO | 00/07226 | 2/2000 |

OTHER PUBLICATIONS

International Search Report for PCT/US2017/058113 dated Feb. 2, 2018.
U.S. Appl. No. 62/364,498 by Measor et al. filed Jul. 20, 2016.

*Primary Examiner* — Laura M Menz
(74) *Attorney, Agent, or Firm* — Ann Marie Mewherter

(57) ABSTRACT

Systems and methods for performing one or more processes on a specimen are provided. One system includes a deposition module incorporated into an existing tool configured to perform an inspection and/or metrology process. The deposition module is configured to deposit one or more materials on a specimen prior to the inspection and/or metrology process performed on the specimen. In some embodiments, the system also includes a stripping module incorporated into the existing tool, and the stripping module is configured to remove material(s) from the specimen subsequent to the inspection and/or metrology process performed on the specimen. The existing tool includes an illumination subsystem configured to direct light having one or more illumination wavelengths to the specimen; a detection subsystem configured to detect light from the specimen; and a computer subsystem configured to determine information for the specimen using output generated by the detection subsystem responsive to the detected light.

22 Claims, 1 Drawing Sheet

(56) References Cited

U.S. PATENT DOCUMENTS

| | | | |
|---|---|---|---|
| 5,614,060 A | 3/1997 | Hanawa | |
| 5,695,568 A | 12/1997 | Sinha et al. | |
| 5,770,099 A | 6/1998 | Rice et al. | |
| 5,849,136 A | 12/1998 | Mintz et al. | |
| 5,882,165 A | 3/1999 | Maydan et al. | |
| 5,910,011 A | 6/1999 | Cruse | |
| 5,926,690 A | 7/1999 | Toprac et al. | |
| 5,935,338 A | 8/1999 | Lei et al. | |
| 5,963,783 A | 10/1999 | Lowell et al. | |
| 5,976,310 A | 11/1999 | Levy | |
| 6,072,147 A | 6/2000 | Koshiishi et al. | |
| 6,074,518 A | 6/2000 | Imafuku et al. | |
| 6,083,363 A | 7/2000 | Ashtiani et al. | |
| 6,089,181 A | 7/2000 | Suemasa et al. | |
| 6,103,014 A | 8/2000 | Lei et al. | |
| 6,110,287 A | 8/2000 | Arai et al. | |
| 6,112,697 A | 9/2000 | Sharan et al. | |
| 6,114,216 A | 9/2000 | Yieh et al. | |
| 6,694,284 B1 * | 2/2004 | Nikoonahad | G01N 21/211 702/155 |
| 7,106,425 B1 * | 9/2006 | Bultman | G01N 21/211 356/237.2 |
| 7,349,090 B2 * | 3/2008 | Wack | G01N 21/211 356/369 |
| 7,460,981 B2 * | 12/2008 | Bultman | G01N 21/211 257/E21.53 |
| 7,541,598 B2 * | 6/2009 | Aasmul | G01J 3/4406 250/458.1 |
| 7,751,046 B2 * | 7/2010 | Levy | G01N 21/211 356/237.1 |
| 8,705,027 B2 | 4/2014 | Lange et al. | |
| 9,425,041 B2 | 8/2016 | Berry, III et al. | |
| 9,431,268 B2 | 8/2016 | Lill et al. | |
| 9,436,094 B2 | 9/2016 | Ueno et al. | |
| 9,451,686 B2 | 9/2016 | Choi | |
| 9,460,974 B1 | 10/2016 | Byun et al. | |
| 9,466,479 B2 | 10/2016 | Von Kanel | |
| 9,466,500 B2 | 10/2016 | Mack et al. | |
| 9,466,524 B2 | 10/2016 | Ma et al. | |
| 9,466,788 B2 | 10/2016 | Deshpande et al. | |
| 9,863,876 B2 * | 1/2018 | Ahner | G01N 21/95 |
| 2006/0072807 A1 | 4/2006 | Bultman et al. | |
| 2007/0126458 A1 | 6/2007 | Shi et al. | |
| 2011/0069313 A1 | 3/2011 | Sakai et al. | |
| 2012/0281275 A1 | 11/2012 | Levy et al. | |
| 2014/0267692 A1 | 9/2014 | Hu-Wei et al. | |
| 2015/0123014 A1 | 5/2015 | Palomba | |
| 2016/0116420 A1 | 4/2016 | Duffy et al. | |
| 2018/0114732 A1 * | 4/2018 | Bell | G01N 21/9501 |

\* cited by examiner

PROCESS MODULES INTEGRATED INTO A METROLOGY AND/OR INSPECTION TOOL

BACKGROUND OF THE INVENTION

1. Field of the Invention

The present invention generally relates to systems and methods for integrating one or more process modules into a metrology and/or inspection tool.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of acceptable semiconductor devices because smaller defects can cause the devices to fail.

The embodiments described herein may improve the sensitivity of defect inspection on patterned surfaces where the patterned structures are not fabricated as intended. The inspection of these surfaces may involve directing light onto such surfaces, collecting light from the surface and processing the collected light to determine whether defects are present. An example of this can be in semiconductor wafer manufacturing where thin-film layers are processed with lithography creating patterns in the surface that are subsequently etched and processed to create semiconductor devices. In the lithography process, a layer of photoresist is deposited on the surface and the photoresist is illuminated with a pattern that is developed and processed to establish a pattern that will be etched into the surface to create a layer for the semiconductor device. Defects within photoresist layers are an example of low-signal producing defects where some amplification of detection signals may be required to adequately identify defects. This need may be higher when considering the extreme ultraviolet (EUV) lithography requirements for detecting printed defects from the mask. Prior methods for accounting for low level signals included optimization of the inspection parameters of light, spectral band, aperture mode and tool speed/pixel to identify an optimal inspection recipe.

However, such optimizations may be insufficient for detecting signal levels on print-check wafers (sometimes called "flop-down wafers") resulting from ever-smaller defects in future design rules (DR) (e.g., a 15 nm DR having allowed excursions of 1/10 of the line width or 1.5 nm) established from EUV mask inspection requirements.

Defect review typically involves re-detecting defects detected as such by an inspection process and generating additional information about the defects at a higher resolution using either a high magnification optical system or a scanning electron microscope (SEM). Defect review is therefore performed at discrete locations on the wafer where defects have been detected by inspection. The higher resolution data for the defects generated by defect review is more suitable fir determining attributes of the defects such as profile, roughness, more accurate size information, etc.

Metrology processes are also used at various steps during a semiconductor manufacturing process to monitor and control the process. Metrology processes are different than inspection processes in that, unlike inspection processes in which defects are detected on a wafer, metrology processes are used to measure one or more characteristics of the wafer that cannot be determined using currently used inspection tools. For example, metrology processes are used to measure one or more characteristics of a wafer such as a dimension (e.g., line width, thickness, etc.) of features formed on the wafer during a process such that the performance of the process can be determined from the one or more characteristics. In addition, if the one or more characteristics of the wafer are unacceptable (e.g., out of a predetermined range for the characteristic(s)), the measurements of the one or more characteristics of the wafer may be used to alter one or more parameters of the process such that additional wafers manufactured by the process have acceptable characteristic(s).

Metrology processes are also different than defect review processes in that, unlike defect review processes in which defects that are detected by inspection are re-visited in defect review, metrology processes may be performed at locations at which no defect has been detected. In other words, unlike defect review, the locations at which a metrology process is performed on a wafer may be independent of the results of an inspection process performed on the wafer. In particular, the locations at which a metrology process is performed may be selected independently of inspection results. In addition, since locations on the wafer at which metrology is performed may be selected independently of inspection results, unlike defect review in which the locations on the wafer at which defect review is to be performed cannot be determined until the inspection results for the wafer are generated and available for use, the locations at which the metrology process is performed may be determined before an inspection process has been performed on the wafer.

Accordingly, it would be advantageous to develop methods and systems for performing one or more processes on a specimen that do not have one or more disadvantages described above.

SUMMARY OF THE INVENTION

The following description of various embodiments is not to be construed in any way as limiting the subject matter of the appended claims.

One embodiment relates to a system configured to perform one or more processes on a specimen that includes a deposition module incorporated into an existing tool configured to perform an inspection and/or metrology process. The deposition module is configured to deposit one or more materials on a specimen prior to the inspection and/or metrology process performed on the specimen. The existing tool includes an illumination subsystem configured to direct light having one or more illumination wavelengths to the specimen; a detection subsystem configured to detect light from the specimen; and a computer subsystem configured to determine information for the specimen using output generated by the detection subsystem responsive to the detected light.

In one embodiment, the one or more materials include one or more sacrificial fluorescing materials not used for fabricating devices on the wafer. In another embodiment, the deposition module is coupled to the existing tool by a common housing, a common wafer handler, a common power source, the computer subsystem, or some combination thereof. In some embodiments, the system also includes a stripping module incorporated into the existing tool, and the stripping module is configured to remove one or more materials from the specimen subsequent to the inspection and/or metrology process performed on the specimen. In a further embodiment, the illumination subsystem comprises a broadband plasma light source. The system may be further configured as described herein.

Another embodiment relates to a method for performing one or more processes on a specimen. The method includes depositing one or more materials on a specimen prior to an inspection and/or metrology process performed on the specimen, and the depositing is performed with a deposition module incorporated into an existing tool configured to perform the inspection and/or metrology process. The method also includes performing the inspection and/or metrology process on the specimen with the existing tool. The existing tool includes an illumination subsystem configured to direct light having one or more illumination wavelengths to the specimen; a detection subsystem configured to detect light from the specimen; and a computer subsystem configured to determine information for the specimen using output generated by the detection subsystem responsive to the detected light.

In one embodiment, the method also includes stripping one or more materials from the specimen subsequent to the inspection and/or metrology process performed on the specimen with a stripping module, and the stripping module is incorporated into the existing tool.

Each of the steps of the method described above may be further performed as described herein. In addition, the method described above may include any other step(s) of any other method(s) described herein. Furthermore, the method described above may be performed by any of the systems described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
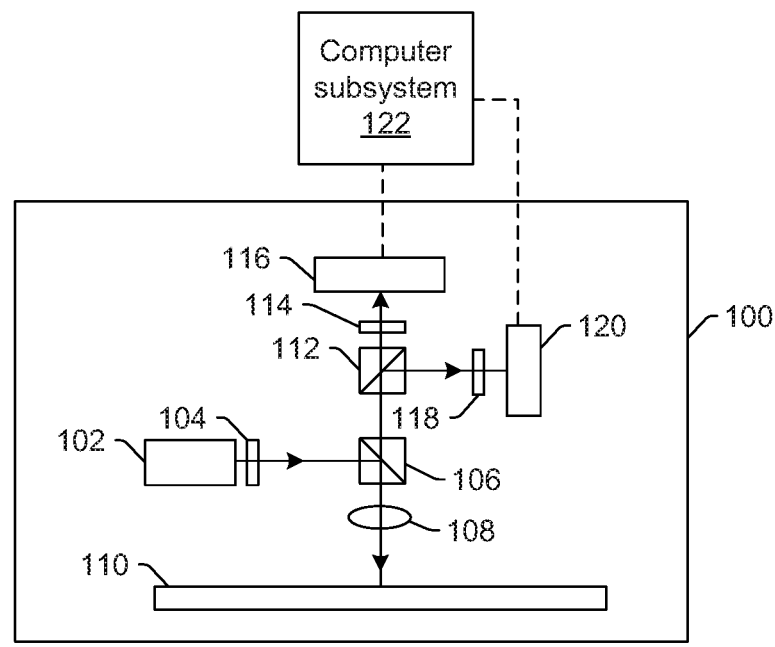
FIG. 1 is schematic diagrams illustrating side views of one embodiment of an existing tool that may be included in the embodiments described herein.

While the invention is susceptible to various modifications and alternative forms, specific embodiments thereof are shown by way of example in the drawings and are herein described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to perform one or more processes on a specimen that includes a deposition module incorporated into an existing tool configured to perform an inspection and/or metrology process. The deposition module is configured to deposit one or more materials on a specimen prior to the inspection and/or metrology process performed on the specimen. The existing tool includes an illumination subsystem configured to direct light having one or more illumination wavelengths to the specimen; a detection subsystem configured to detect light from the specimen; and a computer subsystem configured to determine information for the specimen using output generated by the detection subsystem responsive to the detected light.

In one embodiment, the one or more materials include one or more sacrificial fluorescing materials not used for fabricating devices on the wafer. In another embodiment, the deposition module is coupled to the existing tool by a common housing, a common wafer handler, a common power source, the computer subsystem, or some combination thereof. In some embodiments, the system also includes a stripping module incorporated into the existing tool, and the stripping module is configured to remove one or more materials from the specimen subsequent to the inspection and/or metrology process performed on the specimen. In a further embodiment, the illumination subsystem comprises a broadband plasma light source. The system may be further configured as described herein.

Another embodiment relates to a method for performing one or more processes on a specimen. The method includes depositing one or more materials on a specimen prior to an inspection and/or metrology process performed on the specimen, and the depositing is performed with a deposition module incorporated into an existing tool configured to perform the inspection and/or metrology process. The method also includes performing the inspection and/or metrology process on the specimen with the existing tool. The existing tool includes an illumination subsystem configured to direct light having one or more illumination wavelengths to the specimen; a detection subsystem configured to detect light from the specimen; and a computer subsystem configured to determine information for the specimen using output generated by the detection subsystem responsive to the detected light.

In one embodiment, the method also includes stripping one or more materials from the specimen subsequent to the inspection and/or metrology process performed on the specimen with a stripping module, and the stripping module is incorporated into the existing tool.

The specimens described herein may include wafers or reticles, which may include any wafers and reticles known in the art. In addition, although some embodiments are described herein with respect to a wafer or wafers, it is to be understood that none of the embodiments described herein are limited to a wafer or wafers.

In general, therefore, instead of integrated metrology and inspection, the embodiments described herein integrate one or more process modules on an existing metrology and/or inspection tool. For example, as described further herein, the embodiments may include a deposition module incorporated into an inspector to decorate and improve detection (using a more inspector friendly material). After deposition of the one or more materials, the specimen may be moved to the inspector and/or metrology module. Subsequent to the inspection and/or metrology, the specimen may be processed to remove and/or strip the sacrificial layer. The specimen may also include a wafer in a lot of wafers and only the wafer or wafers in the lot that are to be inspected and/or measured may be processed to form the one or more materials on the wafer or wafers and to remove the one or more materials from the wafer or wafer. In other words, unlike a deposition and/or stripping process that is or are used to fabricate semiconductor devices on a wafer in which one or more materials are formed on all wafers in a lot (or all wafers on which the semiconductor wafers are to be formed), the embodiments described herein may form and remove the one or more materials from only a portion of all wafers (i.e., not all wafers) on which the devices are being formed.

The embodiments described herein may be used to form and remove one or more sacrificial layers from the wafer or wafers that will be inspected and/or measured. The embodiments described herein provide systems and methods to make using such layers easier and faster. The systems described herein can also be used for defect detection and classification based on fluorescence detection from patterned wafers. In addition, the embodiments provide ways to enhance defect detection, characterization, and imaging for patterned wafers by the collection or rejection of fluorescence emitted by defects or patterns under short wavelength excitation.

The existing tool may include an illumination subsystem configured to direct light having one or more illumination wavelengths to a wafer. For example, in the existing tool embodiment shown in FIG. 1, the illumination subsystem of existing tool 100 includes light source 102, which may include any of the light sources described herein. Light generated by light source 102 may be directed through one or more spectral filters 104 of the illumination subsystem. Spectral filter(s) 104 may be configured as described further herein. The illumination subsystem may also include beamsplitter 106 that is configured to reflect light from the spectral filter(s) to objective 108 of the illumination subsystem. Beamsplitter 106 and objective 108 may be further configured as described herein. Objective 108 is configured to focus light having the one or more illumination wavelengths from the beamsplitter to wafer 110, which may include any of the wafers described herein.

The one or more illumination wavelengths may be selected to cause fluorescence from one or more materials on the wafer without causing fluorescence from one or more other materials on the wafer. In this manner, the illumination wavelength range can be adjusted depending on the wafer materials, the patterned structures, and defect composition. The one or more materials may include fluorescing materials such as resist, bottom anti-reflecting coating (BARC), silicon nitride, silicon dioxide, and potentially other materials capable of converting the wavelength of incident light to alternate wavelengths through mechanisms in addition to fluorescence.

In one embodiment, the one or more materials include one or more sacrificial fluorescing materials not used for fabricating devices on the wafer. For example, the one or more materials may include sacrificial fluorescing materials (e.g., resist or BARC) that are used to "decorate" a patterned wafer and that can be removed from the wafer after inspection. In this manner, the sacrificial fluorescing material(s) may not be materials that will form a device structure on the wafer or materials that are used to form a device structure on the wafer. For example, resists are materials that are not normally used to form device structures on wafers while silicon dioxide is a material that is normally used to form device structures on wafers. In other words, resists are materials that do not form final structures in a device while silicon dioxide materials do form final device structures. However, materials such as resists and BARC can be "sacrificial fluorescing materials" as that term is used herein when they are only deposited on wafers to aid in inspection and are removed from the wafers after inspection has been completed. The sacrificial materials may also include materials that are deposited on the wafer, conform to defects, and mask out lower layer structures. The one or more sacrificial materials may also include materials deposited on wafers as described in U.S. Pat. No. 8,705,027 to Lange et al. issued Apr. 22, 2014, which is incorporated by reference as if fully set forth herein. In another embodiment, the invention could also be used in connection with the reverse decoration methods as described in U.S. Patent Application Ser. No. 62/364,498 by Measor et al. filed Jul. 20, 2016, which is incorporated by reference as if fully set forth herein In one embodiment, the illumination subsystem includes a broadband light source and one or more spectral filters positioned in a path of light from the broadband light source. For example, light source 102 shown in FIG. 1 may be a broadband light source, and one or more spectral filters 104 may be positioned in a path of light from the broadband light source. Therefore, the existing tool may include a broadband source with a selectable wavelength range for illumination through wavelength dependent filters. For example, the wavelength(s) directed to the wafer may be altered by changing or removing the spectral filter(s) positioned in the path of the light from the light source. In this manner, the existing tool may be configured to have flexible illumination wavelength(s) that can be varied depending on the materials on the wafer, the fluorescing properties of those materials, and the fluorescing properties of any defects of interest.

The existing tools described herein may also incorporate narrower or modified bandpass filters into the illumination subsystem. In one such embodiment, the one or more spectral filters include one or more interference filters. For example, spectral filter(s) 104 may be interference filter(s). In this manner, the existing tool may include a broadband source with a selectable wavelength range for illumination through interference filters. In addition, a well-defined and selectable illumination wavelength band is preferred, with a reduction of radiation outside the excitation band of at least 7-9 orders of magnitude, and is achievable by the current interference filtering technology available on the market. These filters can complement or replace bandpass filters currently being used in tools. The interference filters can be installed on currently used mechanical assemblies or new mechanical assemblies.

In another embodiment, the illumination subsystem includes one or more narrowband light sources. In an additional embodiment, the illumination subsystem includes one or more laser light sources. The narrowband and/or laser light sources may include any suitable such light sources known in the art. For example, such light sources may include one or more diode lasers, diode-pumped solid state (DPSS) lasers, gas lasers, etc. In addition, the illumination subsystems described herein may include any number of broadband, narrowband, and laser light sources in any suitable combination. Furthermore, as described further herein, the light sources may be quasi-monochromatic light sources. Any of the light sources and illumination subsystem configurations described herein may be included in an inspection system having any suitable configuration (e.g., bright field (BF), dark field (DF), BF and DF, etc.). In one particular example, the illumination subsystem may include only one laser source in a BF inspection system. In another example, an illumination subsystem may include multiple laser sources. Therefore, many different combinations of light sources and inspection system configurations are possible and may be selected depending on, for example, the wafer and/or defect characteristics.

In additional embodiments, the illumination subsystem is configured to direct light having one or more illumination angles and/or one or more illumination polarizations to the wafer, and the one or more illumination angles and/or one or more illumination polarizations are selected to cause more fluorescence, scattered light, or reflected light from the one or more materials on the wafer than from the one or more other materials on the wafer. In other words, the illumination subsystem may be configured to illuminate the wafer with light having polarization(s) and at angle(s) that selectively cause fluorescence or other light from the one or more materials. For instance, different wafer structures may respond differently to light incident from different illumination directions and/or having different polarizations. For example, light having a certain illumination direction, or set of directions, or a certain polarization may penetrate more deeply into a wafer structure and better detect a defect at the bottom of a trench. Alternatively, a certain illumination direction or polarization may not penetrate so deeply and be better suited to detect surface defects. Since the discrimination of defects from background using the various materials' fluorescence properties is a goal of the embodiments described herein, one can see that the combination of illumination direction, polarization, and fluorescence may be important. In other words, the fluorescence techniques described herein may be enhanced if the correct illumination parameters are chosen to complement the desired fluorescence effect.

The illumination subsystem may be configured in a number of different ways for selective illumination angle and/or polarization. For example, the illumination angle may be altered or selected by changing a position of a light source of the illumination subsystem or by controlling one or more other elements of the illumination subsystem that affect the illumination angle. The illumination angle that is altered or selected in the embodiments described herein may be the polar angle and/or the azimuthal angle of the incident light. In addition, the illumination polarization may be selected by selecting a light source that emits light having the selected polarization or by including one or more polarization selection/alteration/filtering elements in the path of the light emitted by the light source.

The existing tool also includes a detection subsystem that may be configured to detect only the fluorescence from the one or more materials or to detect non-fluorescent light from the wafer without detecting the fluorescence from the one or more materials. In this manner, fluorescing defects can be distinguished from non-fluorescing background, and noisy non-fluorescing layers can be filtered out, by collecting only long wavelength light. In the embodiment shown in FIG. 1, the detection subsystem includes objective 108 configured to collect light from wafer 110. In this embodiment, the collected light may include specularly reflected light. However, the collected light may alternatively or additionally include scattered light. The detection subsystem may also include beamsplitter 106 configured to transmit the light collected by the objective lens.

In some cases, the detection subsystem may include beamsplitter 112 configured to transmit light having one or more wavelengths of the light from the wafer, collected by the objective, and transmitted by beamsplitter 106. The detection subsystem may also include one or more bandpass filters 114 that may be configured as described further herein and may transmit light having one or more selected wavelengths. One or more of beamsplitter 106, beamsplitter 112, and bandpass filter(s) 114 may be configured to selectively transmit light having one or more selected wavelengths and to reflect or otherwise block light that does not have the one or more selected wavelengths out of the detection path of the detection subsystem such that they are not detected by detector 116. The one or more selected wavelengths may include wavelengths at which one or more materials on the wafer may fluoresce or wavelengths other than those at which one or more materials on the wafer may fluoresce. In this manner, the detector of the detection subsystem may detect only the fluorescence from the one or more materials or non-fluorescent light from the wafer without detecting the fluorescence from the one or more materials.

In some instances, the detection subsystem may also include one or more bandpass filters 118 and detector 120. In the configuration shown in FIG. 1, light reflected by beamsplitter 112 is directed to one or more bandpass filters 118, and light transmitted by the one or more bandpass filters is detected by detector 120. Bandpass filter(s) 118 and detector 120 may be further configured as described herein. Beamsplitter 112 may be configured to transmit light having one or more first wavelengths and to reflect light having one or more second wavelengths different than the first wavelength(s). In this manner, detectors 116 and 120 may detect light having different wavelengths.

In one embodiment, the illumination and detection subsystems include a common objective lens and a common dichroic mirror or beamsplitter, and the common objective lens and the common dichroic mirror or beamsplitter are configured to direct the light from a light source of the illumination subsystem to the wafer and to direct the fluorescence or the non-fluorescent light from the wafer to a detector of the detection subsystem. For example, as shown in FIG. 1, the illumination and detection subsystems may both include objective 108 making it a common objective lens and beamsplitter 106 making it a common dichroic mirror or beamsplitter. As described above, objective 108 and beamsplitter 106 are configured to direct the light from light source 102 of the illumination subsystem to wafer 110 and to direct the fluorescence or the non-fluorescent light from the wafer to detector 116 and/or detector 120 of the detection subsystem. In this manner, in a fluorescence configuration, light of the excitation wavelength is focused on the specimen through the objective lens after being reflected by an appropriate dichroic mirror or beamsplitter. The fluorescence emitted by the specimen can then be focused to the detector(s) by the same objective and through the same dichroic mirror or beamsplitter. In this way, a relatively high resolution fluorescence image at the selected detection wavelength band and excited by a particular excitation wavelength range can be generated. In addition, any beamsplitters described herein or used in currently available inspection systems can be replaced with dichroic mirrors that reflect certain wavelength bands of light and transmit the corresponding out of band light. Such configurations could increase the amount of light delivered to the wafer and increase the purity of the detected fluorescence signal, rejecting even more of the background generated by the scattered and fluorescence signals outside the spectral band of interest.

In one embodiment, one or more wavelengths of the fluorescence or the non-fluorescent light detected by the detection subsystem are selected by altering one or more parameters of the detection subsystem based on the one or more materials, the defects, the wafer, or some combination thereof. Therefore, like the illumination wavelength range, the detection wavelength range can be adjusted depending on the wafer materials, the patterned structures, and defect composition. The wavelength(s) detected by the detection subsystem may be altered as described herein (e.g., using bandpass filter(s)) or in any other suitable manner known in the art.

In some embodiments, the detection subsystem includes one or more bandpass filters positioned in a path of the fluorescence or the non-fluorescent light from the wafer, and the one or more bandpass filters are configured to control whether the fluorescence or the non-fluorescent light is detected by the detection subsystem. The detection may be preferably performed by inserting specific bandpass filters (such as bandpass filters 114 and/or 118 shown in FIG. 1) with relatively high transmissivity in the desired band and relatively high optical rejection outside the same band (i.e., high out of band extinction) into the imaging or detection path. For example, bandpass filters between the dichroic mirror or beamsplitter described above and the detector can separate excitation light from fluorescent light. Alternatively, fluorescence from a regular wafer pattern could be excluded from the detected image by inserting into the imaging path a bandpass filter centered on the excitation wavelength, which can reduce noise and improve defect capture. In this manner, for defects embedded in regular structures that fluoresce but scatter less than the defects scatter light, insertion into the imaging path of a spectral filter centered on the illumination wavelength that excludes fluorescence emission from the regular wafer pattern may increase the signal-to-noise ratio for the defects. Additionally, the design of these filters will include rejection of stray light sources on the tool, including the auto-focus system and out-of-system-band wavelengths produced by the illuminator. In this way, the detection becomes highly selective and quantitative, augmenting not only the signal-to-noise ratio of the specific defect(s) of interest, but also supplying additional information such as defect material and dimensions as described further herein.

In one embodiment, the detection subsystem includes two or more channels configured to separately and simultaneously detect the fluorescence or the non-fluorescent light from the wafer in different wavelength ranges. For example, the existing tools can be configured to include multiple parallel imaging channels that image varying wavelength ranges through suitable selection of dichroic and bandpass filter components, possibly improving the throughput of the system. In the embodiment shown in FIG. 1, one of the channels may include bandpass filter(s) 114 and detector 116 and the other of the channels may include bandpass filter(s) 118 and detector 120. In addition, the existing tool may include more than two channels (e.g., by insertion of one or more additional beamsplitters (not shown) into the path of the light from the wafer, each of which may be coupled to a detector (not shown) and possibly spectral filters (not shown) and/or other optical elements (not shown)).

In one such embodiment, one of the two or more channels is configured to detect only the fluorescence, and another of the two or more channels is configured to detect the non-fluorescent light from the wafer without detecting the fluorescence. For example, the channel including bandpass filters(s) 114 and detector 116 may be configured to detect only fluorescence from wafer 110, and the channel that includes bandpass filter(s) 118 and detector 120 may be configured to detect the non-fluorescent light from the wafer without detecting the fluorescence. In this manner, one channel may detect fluorescence, and the other channel may detect light other than fluorescence. As such, fluorescence and light other than fluorescence may be detected separately and simultaneously.

In another such embodiment, one of the two or more channels is configured to detect only the fluorescence in a first wavelength band, and another of the two or more channels is configured to detect only the fluorescence in a second wavelength band different than the first wavelength band. For example, the channel including bandpass filters(s) 114 and detector 116 may be configured to detect fluorescence in a first wavelength band, and the channel that includes bandpass filter(s) 118 and detector 120 may be configured to detect fluorescence in a second wavelength band. In this manner, different wavelength ranges of fluorescence may be detected by different channels simultaneously. In addition, the different fluorescence wavelength ranges may be mutually exclusive (e.g., separated by one or more wavelengths) or may overlap entirely (e.g., one wavelength range may be entirely within another wavelength range) or partially (e.g., multiple wavelength ranges may include the same one or more wavelengths, but at least some of the wavelengths in a first wavelength range are mutually exclusive of at least some of the wavelengths in a second wavelength range, and vice versa).

In some embodiments, the detection subsystem includes a spectrometer configured to measure a characteristic of the fluorescence or the non-fluorescent light from the wafer across a wavelength range. For example, in the embodiment shown in FIG. 1, one or more of detectors 116 and 120 may be a spectrometer. In this manner, to further characterize wafer materials by measuring the fluorescence emission spectrum, the existing tool could incorporate a spectrometer possibly for review mode.

As described above, the detection subsystem may be configured to selectively and separately detect the light from the wafer based on the wavelength of the light thereby selectively and separately detecting fluorescence and non-fluorescent light from the wafer. In a similar manner, if the illumination subsystem is configured for selective illumination angle and/or polarization, the detection subsystem may be configured for selective detection of light based on angle from the wafer (or collection angle) and/or polarization. For example, the detection subsystem may include one or more apertures that can be used to control the collection angles of the light detected by the detection subsystem. In another example, the detection subsystem may include one or more polarizing components in the path of the light from the wafer that can be used to control the polarizations of the light detected by the detection subsystem. As described further above, the selective detection of light from the wafer based on illumination angle and/or polarization can be used to complement the separate and selective detection of fluorescence and non-fluorescent light for wafer defect detection.

The existing tool also includes a computer subsystem configured to determine information for defects on the wafer using output generated by the detection subsystem responsive to the detected fluorescence or the detected non-fluorescent light. For example, in the embodiment shown in FIG. 1, the existing tool may include computer subsystem 122, which may be coupled to detectors 116 and 120 by one or more transmission media shown in FIG. 1 by the dashed lines, which may include "wired" and/or "wireless" transmission media, such that the computer subsystem can receive output generated by the detectors of the detection subsystem that is responsive to the detected fluorescence or the detected non-fluorescent light. The output of the detectors may include, for example, signals, images, data, image data, and the like. The computer subsystem may be further configured as described herein. The information may be defects on the wafer, material discrimination, and defect classification. The information may include one or more of data, image data, images, and any other form in which such information can be output. The information may be stored in or output as an inspection results file, defect review results file, or metrology results file.

One main advantage of the embodiments described herein is an augmented capture rate, sensitivity, material discrimination, and classification of the defects of interest for patterned wafer inspection, review, and/or metrology. In one embodiment, the computer subsystem is configured to determine a composition of the defects, the one or more materials, or the wafer based on one or more wavelengths in an emission spectra of the detected fluorescence. For example, in traditional inspection, scattered waves are at the same wavelength as illumination ("elastic scattering"). But in fluorescence, emission occurs at longer wavelengths, allowing potential discrimination of materials with different fluorescent properties. Determining the composition of the one or more materials or the wafer may include monitoring for damage or photo-bleaching of wafers. For example, if the intended composition of one or more materials on a wafer is known to cause the one or more materials to fluoresce, then fluorescence can be used as a measure of the composition of the one or more materials. In particular, photo-bleaching occurs when a fluorescence molecule permanently loses the ability to emit photons under light excitation, i.e., it does not fluoresce any more. Photo-bleaching is due to a photo-induced chemical modification of the fluorescent molecule, either forming covalent bonds with other molecules and/or modifying irreversibly the chemical structure of the original fluorescent molecule due to damage. The amount of excitation-photo emission-decay to ground state cycles is determined by the actual molecular structure and/or by the environment in which the molecule is located. For instance, an environment full of oxygen will increase the probability of photo-bleaching. Therefore, if a material known to fluoresce does not emit any measurable fluorescence, it can be determined that the composition of the material has changed from the intended composition. Quenching is another way in which the amount of fluorescence emitted by a fluorescing molecule is diminished. Quenching is due to either collision with other molecules or forming more stable compounds with other species. In both situations, fluorescence is greatly reduced. As such, if the amount of fluorescence measured for a material is less than expected, the composition of the material may be determined to be different from the intended composition and it may be determined that quenching may have occurred.

In another embodiment, the computer subsystem is configured to determine a composition of the defects, the one or more materials, or the wafer based on a peak intensity of the fluorescence in an emission spectra. For example, fluorescing materials such as oxides, nitrides, and resists have broad emission spectra, but with different peak intensities. Therefore, narrow spectral filtering helps to discriminate the nature of defects, which is related to the specific fabrication process that created them.

In some embodiments, the computer subsystem is configured to detect a defect on the wafer based on the output, determine a width of an emission spectra of the fluorescence corresponding to the defect, and determine a size of the defect based on the width of the emission spectra. For example, the emission spectrum becomes narrower the more a defect approaches the quantum confinement, the more the defect is small, since less excited state is available. Therefore, measuring the width of the spectrum might give an indication of how small the defect is.

In another embodiment, the one or more illumination wavelengths include different excitation wavelengths, and the illumination subsystem is configured to separately direct the different excitation wavelengths to the wafer. For example, the illumination subsystem may include a broadband light source as described above that is configured to generate light at different wavelengths and different excitation wavelengths and one or more spectral filters that can be positioned independently in the path of the light from the light source such that depending on which spectral filter is positioned in the path of the light, different excitation wavelength(s) can be directed to the wafer, one wavelength or wavelength range at a time. In one such embodiment, the detection subsystem is configured to separately detect the fluorescence from the one or more materials due to the different excitation wavelengths, and the computer subsystem is configured to determine a composition of the one or more materials based on which of the different excitation wavelengths caused the fluorescence from the one or more materials. In this manner, the embodiments provide a method for characterizing defect or wafer composition through measurement of the wafer's excitation and emission spectra. For example, the excitation spectrum is different for different materials. Therefore, control of the illumination wavelength range can aid in discrimination of the defect or wafer pattern composition.

In another embodiment, the wafer is a patterned wafer, and the detection subsystem or the computer subsystem is configured to remove output responsive to patterned features on the wafer from the output generated by the detection subsystem. For example, in some instances, the patterned features may not emit fluorescence while defects of interest do. Therefore, by detecting only fluorescence from the wafer, the detection subsystem can remove output responsive to the patterned features from the output. However, in some instances, the detection subsystem or the computer subsystem may be configured to remove the output responsive to the patterned features by Fourier or other spatial filtering that is performed optically by the detection subsystem or electronically by the computer subsystem. Such spatial filtering can be performed in any suitable manner and may be performed in combination with the filtering performed based on the emission wavelength of the detected light thereby reducing noise in the output by a variety of methods.

In some embodiments, the output generated by the detection subsystem includes images of the wafer. For example, the detector(s) of the detection subsystem described above may be imaging detectors that are configured to capture image(s) of the wafer. Therefore, the output generated by the detection subsystem may include images.

In another embodiment, the wafer is a patterned wafer, the defects are fluorescing defects, and the detection subsystem is configured to detect only the fluorescence from the defects on the wafer without detecting the non-fluorescent light from patterned features on the wafer. In this manner, the existing tool can be configured to detect defects on patterned wafers and multiple layer patterned wafers. For example, the existing tool configurations described herein provide control of both the illumination and detection wavelengths primarily to differentiate defects from regular wafer patterns. In one configuration described above, fluorescence from a regular wafer pattern can be excluded from a detected image by inserting into the imaging path a bandpass filter centered on the excitation wavelength. Therefore, one main advantage of the embodiments described herein is an augmented capture rate, sensitivity, material discrimination, and classification of the defects of interest for patterned wafer inspection and review. The embodiments described herein enable detection or rejection of fluorescence with an independent method to remove the contribution of regular patterns from the detected signals or images. Many common wafer materials fluoresce when excited by DUV or UV light, such as resist, BARC, $SiO_2$, and SiN whereas other common wafer materials do not fluoresce or fluoresce minimally, such as metals, Si, and polysilicon. Metals scatter light very efficiently whereas oxides, nitrides, and resists scatter weakly compared to metals. Many inspection points contain multiple layers of varying patterned materials. The embodiments described herein may improve the sensitivity of inspection systems for after develop inspection (ADI) and oxide etch inspections, which are historically difficult for optical inspection methods. For example, one such point, ADI can include inspection of a wafer that has patterned resist on top of transparent films (e.g., BARC and oxide), which in turn lie above a patterned structure that includes metal or semiconductor patterns separated by oxide. Light scattered from the metal lines often dominates signals arising from defects in the resist. Spectrally filtering the light scattered by metals, which has the same wavelength as the illumination, and detecting the fluorescence from the defect can augment the overall signal-to-noise ratio (SNR) and improve defect detection. This method may detect defects embedded in a multi-layer wafer structure if the defect fluoresces and the surrounding wafer structure fluoresces less, as might be the case for resist residues at the bottom of trenches.

An existing tool configured to determine information for defects on a wafer may also be implemented using a quasi-monochromatic light source in the excitation path that illuminates the patterned structure without passing through detection optics (in a dark field like scheme). In this configuration, the excitation dichroic mirror or beamsplitter (e.g., beamsplitter 106) and illumination filters (e.g., spectral filter(s) 104) described above can be removed and the detection objective simplified. Such an existing system may be configured as described in U.S. Patent Application Publication No. 2015/0123014 to Palomba on May 7, 2015, which is incorporated by reference as if fully set forth herein. The embodiments described herein may be further configured as described in this patent application publication.

Such an implementation can be realized on a modified dark field inspection tool such as the 9xxx series of tools, which are commercially available from KLA-Tencor, if the collection optics of such tools were modified to accommodate a broader wavelength range. The existing tools described herein can also be configured for a dark field flood illumination imaging system. For this concept, because fluorescence frequently occurs at wavelengths longer than 250 nm, the imaging objective may be easier and cheaper to manufacture compared to broadband DUV objectives. Along these lines, platforms of commercially available existing tools such as the 236x tools commercially available from KLA-Tencor could be modified to include outside the objective illumination using DUV and UV laser sources. This would limit selecting the illumination wavelength based on the excitation spectra of the material, but it could increase the amount of light delivered to the wafer resulting in an increase in the fluorescence signal.

It is noted that FIG. 1 is provided herein to generally illustrate some configurations of the existing tool embodiments described herein. Obviously, the existing tool configurations described herein may be altered to optimize the performance of the system as is normally performed when designing a commercial inspection, review, and/or metrology tool. In addition, the existing tools described herein may be implemented using an existing inspection system (e.g., by adding functionality described herein to an existing inspection system) such as the 29xx/28xx and 236x series of tools that are commercially available from KLA-Tencor. For some such systems, the methods described herein may be provided as optional functionality of the existing tool (e.g., in addition to other functionality of the existing tool). Alternatively, the existing tool described herein may be designed "from scratch" to provide a completely new system.

The existing tools described above may be, therefore, different from some currently available wafer inspection systems in a number of important ways. For example, some currently available inspection systems contain spectral filters to either detect or suppress fluorescence signals from defects or wafer background respectively. These tools are configured for only a single illumination wavelength and contain a limited selection of spectral filters in the collection path. Generally, the tools contain two collection path filters: one filter that passes only the illumination wavelength to exclude fluorescence from the wafer background and one filter that blocks the illumination wavelength to enable detection of fluorescence from defects.

Some inspection tools are also limited in their ability to remove contributions from rectilinear patterns from the detected signals. Furthermore, some inspection tools do not provide high resolution microscopic imaging. While some tools are designed to remove regular wafer patterns from images (e.g., die-to-die or cell-to-cell subtraction or Fourier filtering), these tools are currently not configured to detect only or exclude only fluorescence from either defects or regular patterns. In addition, although some inspection systems are configured to detect fluorescence signals instead of signals at the wavelength of illumination, such systems are not configured to detect fluorescence signals from defects to improve signal-to-noise, where noise originates from non-fluorescing regular wafer structures. In addition, many systems are not configured for tuning the incident waveband or measuring the emission spectra to determine wafer or defect composition.

Although the existing tool has been described herein as being a light-based or optical existing tool, it is to be understood that the existing tool may be configured to also or alternatively to use a different type of energy to perform the one or more processes described herein (e.g., inspection, review, and metrology). For example, the existing tool may be an electron beam-based tool such as a scanning electron microscope (SEM) or a transmission electron microscope (TEM) and/or a charged particle beam-based tool such as a focused ion beam (FIB) tool. Such existing systems may include any suitable commercially available system for processing a wafer or reticle.

Figure 2:
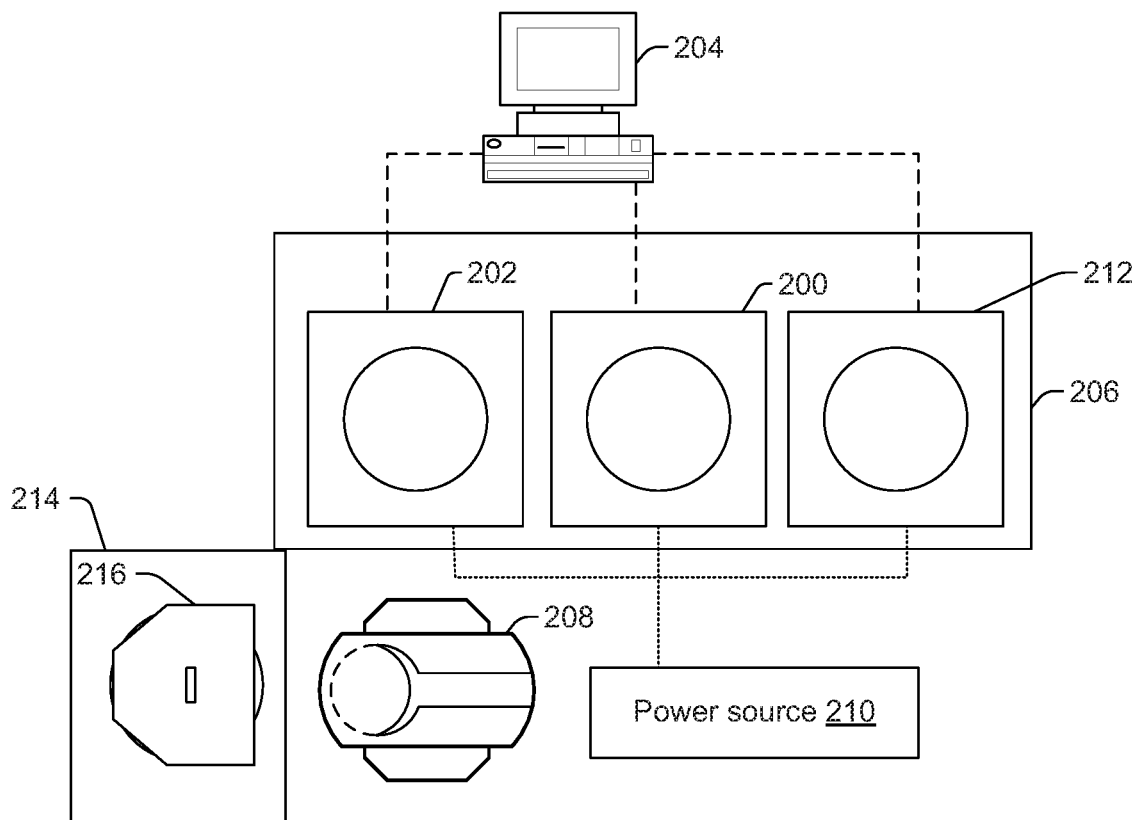
FIG. 2 is a schematic diagram illustrating a plan view of one embodiment of a system embodiment configured as described herein.

FIG. 2 illustrates one embodiment of a system described herein for performing one or more processes on a specimen. The one or more processes may include a deposition process such as one of those described herein, a measurement and/or inspection process, and optionally a stripping process. The system includes deposition module 202 incorporated into existing tool 200 configured to perform an inspection and/or metrology process. The existing tool may be configured as described further herein. For example, the existing tool includes an illumination subsystem configured to direct light having one or more illumination wavelengths to the specimen; a detection subsystem configured to detect light from the specimen; and computer subsystem 204 configured to determine information for the specimen using output generated by the detection subsystem responsive to the detected light. In a further embodiment, the illumination subsystem comprises a broadband plasma light source, which may include any suitable such light source known in the art.

The information may include information for defects detected on the specimen during an inspection process, information for one or more measurements performed on the specimen during a metrology process, and any other information that can be generated by the existing tools described herein. The measurement processes and existing tool may be further configured as described in U.S. Patent Application Publication No. 2016/0116420 published on Apr. 28, 2016 to Duffy et al., which is incorporated by reference as if frilly set forth herein. The embodiments described herein may be further configured as described in this patent application.

The deposition module is configured to deposit one or more materials on a specimen prior to the inspection and/or metrology process performed on the specimen. In one embodiment, the one or more materials include one or more sacrificial fluorescing materials not used for fabricating devices on the wafer. The one or more sacrificial fluorescing materials may include any of the material(s) described herein.

The deposition module may be configured to deposit the one or more materials on the specimen as described in U.S. Pat. No. 8,705,027 to Lange et al. issued Apr. 22, 2014, which is incorporated by reference as if fully set forth herein. The deposition module may be a chemical vapor deposition module or a physical vapor deposition module configured to deposit any of the materials described herein on the specimen. The deposition module may also include any suitable deposition module configured to deposit one or more materials on a specimen such as a wafer or a reticle. Examples of suitable deposition modules are illustrated in U.S. Pat. No. 4,232,063 to Rosler et al., U.S. Pat. No. 5,695,568 to Sinha et al., U.S. Pat. No. 5,882,165 to Maydan et al., U.S. Pat. No. 5,935,338 to Lei et al., U.S. Pat. No. 5,963,783 to Lowell et al., U.S. Pat. No. 6,103,014 to Lei et al., U.S. Pat. No. 6,112,697 to Sharan et al., and U.S. Pat. No. 6,114,216 to Yieh et al., and PCT Application Nos. WO 99/39183 to Gupta et al., WO 00/07226 to Redinbo et al., and are incorporated by reference as if fully set forth herein. Additional examples of suitable deposition modules are described in U.S. Pat. No. 9,460,974 to Byun et al. issued on Oct. 4, 2016, U.S. Pat. No. 9,466,479 to Von Kanel issued on Oct. 11, 2016, U.S. Pat. No. 9,466,500 to Mack et al, issued on Oct. 11, 2016, and U.S. Pat. No. 9,466,524 to Ma et al. issued on Oct. 11, 2016, which are incorporated by reference as if fully set forth herein. The deposition module may be further configured as described in any of these patents and publications.

In some embodiments, the system also includes stripping module 212 incorporated into existing tool 200, and the stripping module is configured to remove one or more materials from the specimen subsequent to the inspection and/or metrology process performed on the specimen. The stripping module may include any suitable stripping and/or etch tool known in the art. Examples of suitable etch tools are illustrated in U.S. Pat. No. 4,842,683 to Cheng et al., U.S. Pat. No. 5,215,619 to Cheng et al., U.S. Pat. No. 5,614,060 to Hanawa, U.S. Pat. No. 5,770,099 to Rice et al., U.S. Pat. No. 5,882,165 to Maydan et al., U.S. Pat. No. 5,849,136 to Mintz et al., U.S. Pat. No. 5,910,011 to Cruse, U.S. Pat. No. 5,926,690 to Toprac et al., U.S. Pat. No. 5,976,310 to Levy, U.S. Pat. No. 6,072,147 to Koshiishi et al., U.S. Pat. No. 6,074,518 to Imafuku et al., U.S. Pat. No. 6,083,363 to Ashtiani et al., U.S. Pat. No. 6,089,181 to Suemasa et al., U.S. Pat. No. 6,110,287 to Arai et al., U.S. Pat. No. 9,425,041 to Berry, III et al. issued on Aug. 23, 2016, U.S. Pat. No. 9,431,268 to Lill et al. issued on Aug. 30, 2016, U.S. Pat. No. 9,436,094 to Ueno et al. issued on Sep. 6, 2016, U.S. Pat. No. 9,451,686 to Choi issued on Sep. 20, 2016, and U.S. Pat. No. 9,466,788 to Deshpande et al. issued on Oct. 11, 2016, which are incorporated by reference as if fully set forth herein. The embodiments described herein may be further configured as described in any of these patents.

In another embodiment, the deposition module is coupled to the existing tool by common housing 206, common wafer handler 208, common power source 210, computer subsystem 204, or some combination thereof. The common housing may have any suitable configuration known in the art. For example, the original housing of the existing tool may simply be expanded to accommodate the deposition module. In this manner, the existing tool and the deposition module may be configured as a single unit or tool. The common wafer handler may include any suitable mechanical and/or robotic assembly known in the art. The common wafer handler may be configured to move the specimens between the existing tool and the deposition module in such a way that a specimen can be moved from the deposition module directly into the existing tool without having to put the specimen back into its cassette or other container between the processes. The common power source may include any suitable power source known in the art. The computer subsystem may be coupled to the existing tool as described further herein as well as to the deposition module such that the computer subsystem can interact with the deposition module (e.g., to control one or more deposition processes that are performed in the deposition module). The stripping module may be coupled to the existing tool in the same manner or manners if it is included in the system.

The hardware of the existing tool may be disposed in a measurement chamber, that is separate from the deposition model and stripping module included in the system. The measurement chamber may be disposed laterally or vertically proximate the deposition model and stripping module. For example, the system may be configured as a cluster of modules that may each be configured to perform substantially similar processes or different processes. In addition, the measurement chamber and the deposition and stripping modules may disposed laterally or vertically proximate a load chamber 214 of the system. The load chamber may be configured to support multiple specimens such as cassette 216 of wafers that are to be processed in the system. Robotic wafer handler 208 may be configured to remove a specimen from the load chamber prior to processing and measurement and/or inspection and to dispose a processed specimen into the load chamber. Furthermore, the deposition and stripping modules may be disposed in other locations proximate the measurement chamber such as anywhere proximate the measurement chamber where there is sufficient space for the modules and anywhere a robotic wafer handler may fit such that a specimen may be moved between a measurement chamber and the modules.

In this manner, robotic wafer handler 208 of the existing tool, a stage (not shown), or another suitable mechanical device may be configured to move a specimen to and from the measurement chamber and process modules of the system. In addition, the robotic wafer handler, the stage, or another suitable mechanical device may be configured to move specimen 246 between process modules of the system and the measurement chamber.

Each of the system embodiments described above may be configured to perform any step(s) of any method(s) described herein. In addition, each of the system embodiments described herein may be configured according to any other embodiments or systems described herein.

Another embodiment relates to a method for performing one or more processes on a specimen. The method includes depositing one or more materials on a specimen prior to an inspection and/or metrology process performed on the specimen, and the depositing is performed with a deposition module incorporated into an existing tool configured to perform the inspection and/or metrology process. The method also includes performing the inspection and/or metrology process on the specimen with the existing tool. The existing tool includes an illumination subsystem configured to direct light having one or more illumination wavelengths to the specimen; a detection subsystem configured to detect light from the specimen; and a computer subsystem configured to determine information for the specimen using output generated by the detection subsystem responsive to the detected light.

In one embodiment, the method also includes stripping one or more materials from the specimen subsequent to the inspection and/or metrology process performed on the specimen with a stripping module, and the stripping module is incorporated into the existing tool.

Each of the embodiments of the method described above may include any other step(s) of any other method(s) described herein. In addition, each of the embodiments of the method described above may be performed by any of the systems described herein.

Another embodiment relates to a non-transitory computer-readable medium containing program instructions stored therein for causing a computer system to perform a computer-implemented method for performing one or more processes on a specimen. One embodiment of such a computer-readable medium contains program instructions stored therein for causing a computer system to perform a computer-implemented method for performing one or more processes on a specimen. The computer-implemented method includes any step(s) described above with respect to the computer subsystem of the system. In addition, the computer-readable medium may be further configured as described herein.

Program instructions implementing methods such as those described herein may be stored on the computer-readable medium. The computer-readable medium may be a non-transitory computer-readable storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, mainframe computer system, workstation, image computer, parallel processor, or any other device known in the art. In general, the term "computer system" may be broadly defined to encompass any device having one or more processors, which executes instructions from a memory medium.

Further modifications and alternative embodiments of various aspects of the invention will be apparent to those skilled in the art in view of this description. For example, systems and methods for performing one or more processes on a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to perform one or more processes on a specimen, comprising:
    a deposition module incorporated into an existing tool configured to perform an inspection and/or metrology process, wherein the deposition module is configured to deposit one or more materials on a specimen prior to the inspection and/or metrology process performed on the specimen; and
    wherein the existing tool comprises:
        an illumination subsystem configured to direct light having one or more illumination wavelengths to the specimen;
        a detection subsystem configured to detect light from the specimen; and
        a computer subsystem configured to determine information for the specimen using output generated by the detection subsystem responsive to the detected light.

2. The system of claim 1, wherein the one or more materials comprise one or more sacrificial fluorescing materials not used for fabricating devices on the wafer.

3. The system of claim 1, wherein the deposition module is coupled to the existing tool by a common housing, a common wafer handler, a common power source, the computer subsystem, or some combination thereof.

4. The system of claim 1, further comprising a stripping module incorporated into the existing tool, wherein the stripping module is configured to remove one or more materials from the specimen subsequent to the inspection and/or metrology process performed on the specimen.

5. The system of claim 1, wherein the illumination subsystem comprises one or more of: a broadband plasma light source, a laser source providing line illumination, or a laser source providing one or more scanning spots.

6. A method for performing one or more processes on a specimen, comprising:
    depositing one or more materials on a specimen prior to an inspection and/or metrology process performed on the specimen, wherein said depositing is performed with a deposition module incorporated into an existing tool configured to perform the inspection and/or metrology process; and
    performing the inspection and/or metrology process on the specimen with the existing tool, wherein the existing tool comprises:

an illumination subsystem configured to direct light having one or more illumination wavelengths to the specimen;

a detection subsystem configured to detect light from the specimen; and a computer subsystem configured to determine information for the specimen using output generated by the detection subsystem responsive to the detected light.

7. The method of claim 6, further comprising stripping one or more materials from the specimen subsequent to the inspection and/or metrology process performed on the specimen with a stripping module, wherein the stripping module is incorporated into the existing tool.

8. The method of claim 7, wherein the specimen is one of multiple specimens in a lot, and wherein said stripping is not performed for all of the multiple specimens in the lot.

9. The method of claim 6, wherein the specimen is one of multiple specimens in a lot, and wherein said depositing is not performed for all of the multiple specimens in the lot.

10. The method of claim 6, wherein performing the inspection and/or metrology process on the specimen with the existing tool comprises detecting fluorescence from the specimen and detecting defects on the specimen based on the detected fluorescence.

11. The method of claim 6, wherein performing the inspection and/or metrology process on the specimen with the existing tool comprises detecting fluorescence from the specimen and classifying defects on the specimen based on the detected fluorescence.

12. The method of claim 6, wherein performing the inspection and/or metrology process on the specimen with the existing tool comprises rejecting fluorescence emitted by defects or patterns on the specimen under short wavelength excitation.

13. A method for performing one or more processes on a specimen, comprising:

incorporating a deposition module into an existing tool configured to perform an inspection and/or metrology process on a specimen;

depositing one or more materials on the specimen with the deposition module prior to the inspection and/or metrology process performed on the specimen; and performing the inspection and/or metrology process on the specimen with the existing tool, wherein performing the inspection and/or metrology process on the specimen comprises:

directing light having one or more illumination wavelengths to the specimen with an illumination subsystem of the existing tool;

detecting light from the specimen with a detection subsystem of the existing tool; and determining information for the specimen with a computer subsystem of the existing tool using output generated by the detection subsystem responsive to the detected light.

14. The method of claim 13, wherein the one or more materials comprise one or more sacrificial fluorescing materials not used for fabricating devices on the wafer.

15. The method of claim 13, wherein incorporating the deposition module into the existing tool comprises coupling the deposition module to the existing tool by a common housing, a common wafer handler, a common power source, the computer subsystem, or some combination thereof.

16. The method of claim 13, wherein the illumination subsystem comprises one or more of: a broadband plasma light source, a laser source providing line illumination, or a laser source providing one or more scanning spots.

17. The method of claim 13, further comprising incorporating a stripping module into the existing tool and removing one or more materials from the specimen with the stripping module subsequent to the inspection and/or metrology process performed on the specimen.

18. The method of claim 17, wherein the specimen is one of multiple specimens in a lot, and wherein said removing is not performed for all of the multiple specimens in the lot.

19. The method of claim 13, wherein the specimen is one of multiple specimens in a lot, and wherein said depositing is not performed for all of the multiple specimens in the lot.

20. The method of claim 13, wherein performing the inspection and/or metrology process on the specimen with the existing tool further comprises detecting fluorescence from the specimen and detecting defects on the specimen based on the detected fluorescence.

21. The method of claim 13, wherein performing the inspection and/or metrology process on the specimen with the existing tool further comprises detecting fluorescence from the specimen and classifying defects on the specimen based on the detected fluorescence.

22. The method of claim 13, wherein performing the inspection and/or metrology process on the specimen with the existing tool further comprises rejecting fluorescence emitted by defects or patterns on the specimen under short wavelength excitation.

* * * * *